US00PP35797P2

(12) United States Plant Patent
Hansen

(10) Patent No.: US PP35,797 P2
(45) Date of Patent: May 7, 2024

(54) ***BAPTISIA* PLANT NAMED 'PERIWINKLE POPSICLE'**

(50) Latin Name: ***Baptisia* hybrid**
Varietal Denomination: Periwinkle Popsicle

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,348

(22) Filed: Jul. 25, 2023

(51) Int. Cl.
*A01H 5/02* (2018.01)
*A01H 6/54* (2018.01)

(52) U.S. Cl.
USPC ..... Plt./263.1

(58) Field of Classification Search
USPC ..... Plt./263.1, 226
CPC ..... A01H 5/02; A01H 5/00; A01H 6/54
See application file for complete search history.

(56) References Cited

U.S. PATENT DOCUMENTS

PP33,234 P2 * 7/2021 Hansen ..... Plt./263.1

* cited by examiner

*Primary Examiner* — June Hwu

(57) ABSTRACT

A new and distinct plant cultivar of hardy herbaceous False Indigo plant named *Baptisia* 'Periwinkle Popsicle' is characterized by flowers that open up dark blue beginning in late May and continuing for two to three weeks. The new plant has a narrow, tall, upright, vase-shaped, multi-stemmed, winter-hardy habit with glaucous dark-green tri-foliate foliage and is suitable for landscaping as a specimen or en masse.

2 Drawing Sheets

Botanical classification: *Baptisia* hybrid.
Cultivar designation: 'Periwinkle Popsicle'.

STATEMENT REGARDING PRIOR DISCLOSURES UNDER 37 CFR 1.77(B)(6)

*Baptisia* 'Periwinkle Popsicle' was promoted with a brief description and photographs on a website operated by Walters Gardens, Inc. on Dec. 1, 2022, followed by the "Walters Gardens 23-24 Catalog" initially distributed by Walters Gardens, Inc. on May 19, 2023. The first offer for sale was on Aug. 9, 2022, and the first enabling disclosure of *Baptisia* 'Periwinkle Popsicle', in the form of a sale, was made by Walters Gardens, Inc. on May 1, 2023, to Pender Pines Garden Center. The information and plants for this sale and all sales thereafter were obtained from the inventor. No plants of *Baptisia* 'Periwinkle Popsicle' have been sold or offered for sale, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of hybrid *Baptisia* plant, botanically known as *Baptisia* 'Periwinkle Popsicle' and will be referred to hereafter by its cultivar name, 'Periwinkle Popsicle', and the new plant. The new plant represents a new false indigo, a hardy herbaceous perennial grown for landscape and cut flower use.

'Periwinkle Popsicle' arose from an ongoing breeding program of the inventor at a nursery in Waseca, Minnesota with continued evaluation at a wholesale perennial nursery in Zeeland, Michigan with the specific intention of improving garden worthiness of perennial false indigo plants with a wider variety of flower colors and improved garden habit.

The new plant was a single seedling selection from a presumed self-pollination of a proprietary unreleased hybrid selection of *Baptisia alba* times a proprietary unreleased hybrid selection of *Baptisia minor* (not patented). Seeds were collected from the individual selected female plant in fall of 2009 at the isolation block in Waseca, Minnesota, USA by the inventor. The seeds were sown by the inventor at a wholesale perennial nursery in Zeeland, Michigan in the fall of 2009 and the initial selection made in the spring of 2011 at the same nursery in Zeeland and given the breeder code H9-52-01.

'Periwinkle Popsicle' was initially asexually propagated by stem cuttings at a wholesale perennial nursery in Zeeland, Michigan in 2016. The resultant plants have demonstrated that the new plant has remained stable and true to type in successive generations of asexual propagation.

The nearest comparison plants known to the inventor are: 'Blueberry Sundae' U.S. Plant Pat. No. 23,891 'Blue Bubbly' U.S. Plant Pat. No. 33,234, 'Grape Taffy' U.S. Plant Pat. No. 26,587, 'Lavender Stardust' (U.S. Plant patent application Ser. No. 15/530,089, abandoned), 'Sparkling Sapphires' U.S. Plant Pat. No. 27,904, and 'Violet Dusk' U.S. Plant Pat. No. 32,553.

'Blueberry Sundae' has a shorter habit and flowers that are indigo-blue. 'Blue Bubbly' is taller, more vase-shaped in habit and flowers are lavender-blue with cream-colored keels. 'Grape Taffy' has a much shorter and more compact in habit and the flowers are reddish-purple with a buff-yellow keel. 'Lavender Stardust' has a similar habit with lilac-purple flowers having a soft yellow keel, and the flowers and foliage are smaller. 'Sparkling Sapphires' has a much smaller compact habit with violet-blue flowers and pale-yellow keels. 'Violet Dusk' has a more mounded and less vase-shaped habit, is slightly smaller in height and width, and the flowers are lavender-violet with cream-colored keels.

The mother plant has flowers that are not as deeply colored on shorter scapes, and shorter habit, and the flowers open at the same time as the foliage is developed.

The new plant differs from all *Baptisia* known to the inventor in the following combined traits:

1. Flowers open dark blue and retain their color through the effective season;
2. Flowering begins late-May in Michigan and continues for about two to three weeks;
3. Narrow, tall-height, upright, vase-shaped, multi-stemmed, winter-hardy habit;
4. Glaucous, dark-green, tri-foliate foliage.

BRIEF DESCRIPTION OF THE DRAWINGS

The photographs of 'Periwinkle Popsicle' demonstrate the unique traits of the new plant and the overall appearance. The colors are as accurate as reasonably possible with color reproductions. Variations in ambient light spectrum, source, and direction may cause the appearance of minor variations in color. The accompanying photograph is of a six-year-old plant growing in an open full-sun trial garden in Zeeland, Michigan.

DETAILED BOTANICAL DESCRIPTION OF THE PLANT

Figure 1:
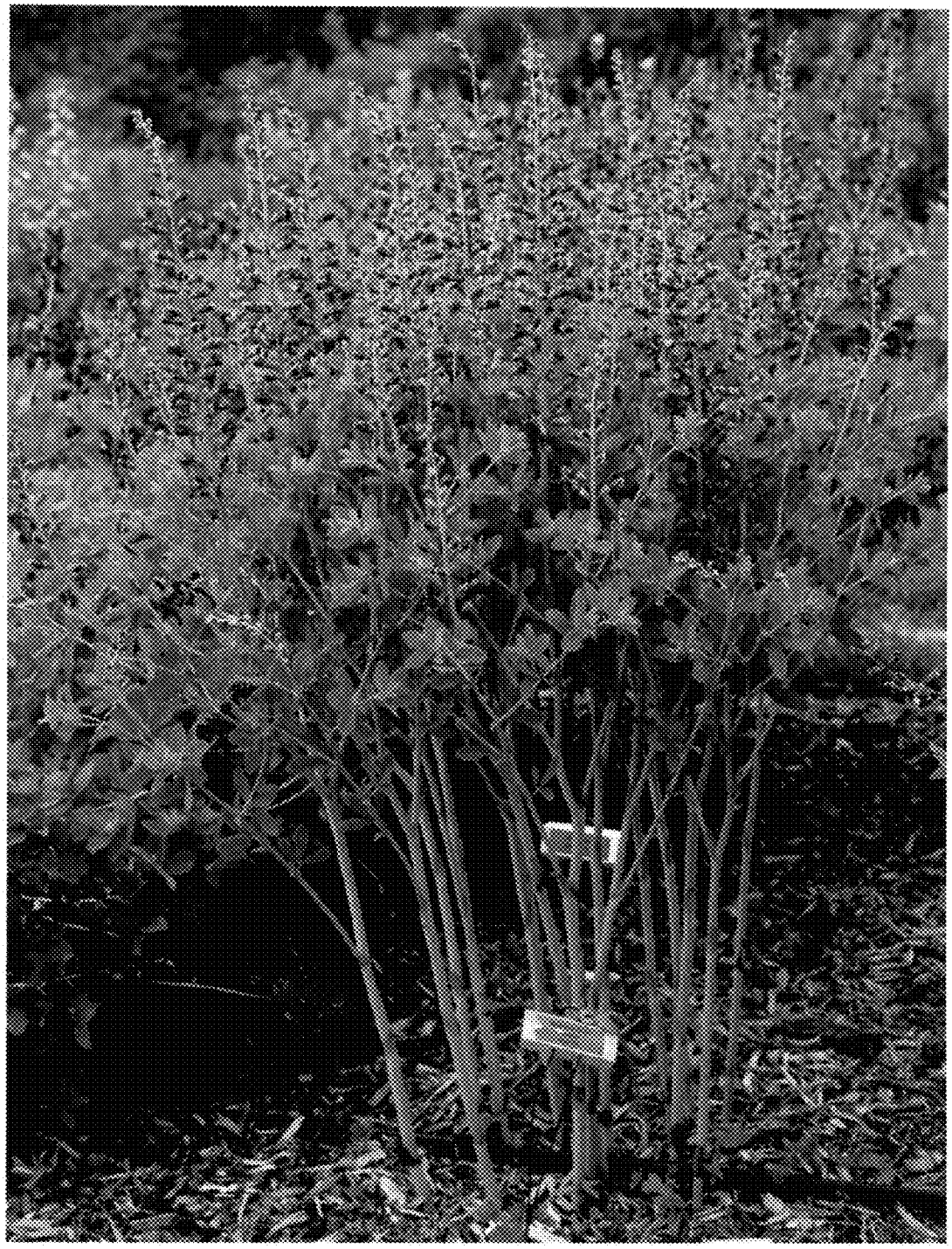
FIG. 1 shows the habit of a plant in full flower.
Figure 2:
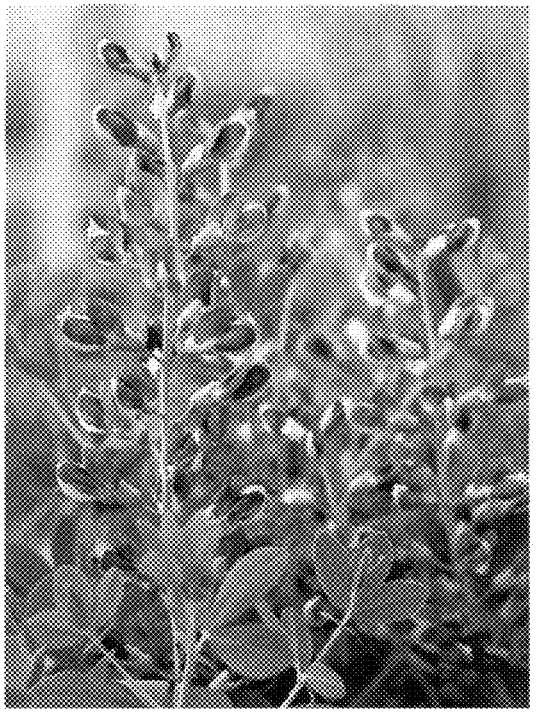
FIG. 2 shows a close-up of the inflorescence with flowers and buds.
Figure 3:
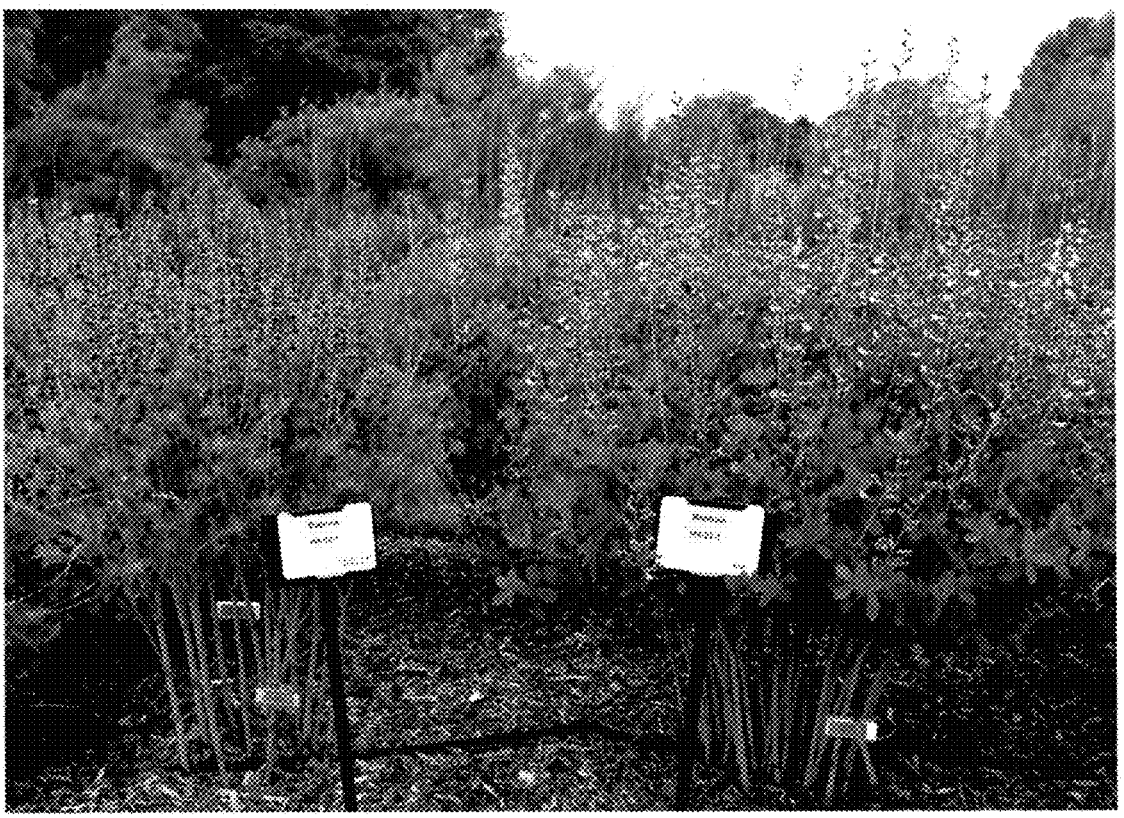
FIG. 3 shows a comparison with 'Periwinkle Popsicle' on the left and 'Blue Bubbly' on the right.

The following is a detailed description of six and ten-year-old plants of 'Periwinkle Popsicle' as grown outdoors in a trial block at a wholesale perennial nursery in Zeeland, Michigan. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, tall, well-branched, many-stemmed, rounded growth habit with long inflorescences held above the foliage;

Plant size: Stems and crown about 39 cm across at soil level, at flowering about 104 cm tall from soil to top of flowers and 95 cm wide just below initial flowers; at maturity plant foliage height about 100 cm tall and about 95 cm wide;

Roots: Fibrous, well-branched, long, deeply rooted;

Root color: Nearest RHS 161D;

Propagation method: Stem cuttings, rooting in about three weeks;

Growth rate: Moderate to average;

Stems: Rigid and upright; highly glaucous; glabrous; cylindrical; smooth; lower two to three nodes without leaves or branches; normally two to three branches per plant below flowers; about 32 stems per clump;

Stem size: Main stem to about 15 mm diameter at base and 105 cm tall, average about 98 cm long and about 11 mm diameter; to about 28 cm long from soil to below initial flowers;

Stem branches: Primary branches at about a 45-degree angle above horizontal, up to 63 cm long and 9 mm diameter, average for primary branches about 42 cm long and 7 mm diameter, smaller distally; and two to four alternate secondary branches per stem of about 42 cm long and 4 mm diameter, averaging about 30 cm long and 3.5 mm diameter;

Stem color: Nearest RHS 147D;

Stem scales: At stem nodes; broadly ovate; emarginate to retuse apex with sharply pointed sides; truncate clasping base; margin entire; dehiscing to leave behind thin scar on stem; about 18 mm wide at base and 30 mm wide in center; about 32 mm long and 2 mm wide in center of apex;

Stem scale color: Variable, nearest RHS N186A, RHS 148C, and between RHS 146B and RHS 147B before dehiscing;

Internodes: Up to 14 cm apart between lowest branches, average about 9 cm;

Internode color: Between RHS 138D and RHS 148D with frequent marks of nearest RHS N186A, with scale scar at node nearest RHS 202A;

Foliage: Alternate; ternate to palmately compound with three leaflets; outer two leaflets independent, at nearly 80-degree angle to middle leaflet; up to 4.7 cm long and 8.2 cm wide;

Leaflet: Three; oblanceolate; broadly apex acute; base cuneate; margins entire; petiolate; adaxial and abaxial surfaces matte, glabrous; moderately glaucous adaxial and abaxial; middle lobe to about 4.5 cm long and 2.1 cm wide, side lobes about 4.4 cm long and 1.8 cm wide;

Leaflet color: Newly expanding adaxial between RHS 138A and RHS 146A, abaxial between RHS 138A and RHS 146B; mature adaxial between RHS 137A and RHS 189A, abaxial between RHS 137B and RHS 189A;

Venation: Pinnate, glabrous, thin, not conspicuous;

Vein color: Newly expanding foliage adaxial midrib nearest RHS 146C and secondary adaxial veins between RHS 138A and RHS 146A, abaxial midrib nearest RHS 146C, and secondary abaxial veins between RHS 138A and RHS 146B; mature adaxial midrib nearest RHS 137A and secondary veins nearest RHS 137A, abaxial midrib between RHS 145C and RHS 146D and secondary veins same nearest RHS 146B;

Petioles: Glabrous; glaucous; concavo-convex; to about 8 mm long and 3 mm wide at partially clasping base, average 6 cm long and 2.5 mm wide;

Petiole color: Adaxial nearest RHS 145A, abaxial nearest RHS 145A;

Stipules: Narrowly lanceolate, acute apex with base truncate; to about 20 mm long and 10 mm wide, average 18 mm long and 9 mm wide with largest stipules below primary branches and decreasing distally and on secondary branches;

Stipule color: Nearest RHS 138A on both surfaces;

Peduncle: Cylindrical with vertical shallow ridges and furrows; glaucous; glabrous; from first flower to apex about 51 cm long; diameter at the base of first flower about 6 mm and about 2 mm diameter at the apex;

Peduncle color: Nearest RHS 146A in the flowering portions;

Pedicel: Cylindrical, glabrous, glaucous; about 6 mm long and 1 mm diameter;

Pedicel color: Between RHS 145A and RHS 146D ventrally and dorsally nearest RHS 146C with light blush of nearest RHS 79A;

Calyx: Campanulate; five-lobed; to about 10 mm long, 7 mm tall, and 6 mm across at apex;

Sepals: Five; two dorsal, one ventral, and two lateral; acute apices; entire margins; fused base; dorsal sepals divided 1 mm between each other and 3 mm between lateral sepals; notched about 1 mm deep with lobes acute; other three sepals with acute apices; ventral sepal divided about 2 mm between lateral sepals; glabrous adaxial and abaxial; glaucous abaxial and matte adaxial; dorsal sepals to about 9 mm long and 2 mm wide at fusion; other three sepals to about 9 mm long and 3 mm across at fusion;

Sepal color: Adaxial nearest RHS 146C with light blush of nearest RHS N79A; abaxial between RHS 146B and RHS 146C variably blushed with nearest RHS N79A;

Buds one day prior to anthesis: Obovoid, slightly flatted vertically; to about 22 mm long, 8 mm tall, and 10 mm wide, slightly smaller in distal flowers;

Bud color: One day prior to opening exposed keel petal nearest RHS 145D, enfolded banner petal proximally nearest RHS N92A and distally between RHS 90D and RHS 92A, exposed alae petals between RHS 90D and RHS 92A;

Flower: Zygomorphic; papilionaceous; non-secund; held at about 45-degree angle above horizontal; to about 82 flowers per center panicle stem and about 32 flowers per primary branch; seasonally effective for about 2 weeks beginning in late May in Zeeland, MI; individual flowers remain effective and on raceme for about four days; individually to about 22 mm long, 10 mm tall, and 15 mm wide at largest portions; consisting of an upper banner reflexing with maturity, a lower keel made up of two lobes folded around gynoecium and androecium; and two lateral wings or alae laterally appressed against keel;

Flower fragrance: None detected;

Petals: Five; with a lower fused keel, an upper banner, and two lateral wings or alae; keel comprised of two sections that are folded around stamens and pistil;

*Banner petal*.—Conduplicate, reflexed upward and backward with maturity, and pinched in the middle; apex retuse, with apex notched about 2 mm deep; base claw-like, margin entire; to about 16 mm long, 10 mm across natural width, 17 mm wide flattened spread and 7 mm tall; basal portion attenuate claw-like, 5 mm long and 5 mm wide distally and 1 mm wide at base.

*Banner color*.—Adaxial between RHS 93C and RHS 93D finely maculate toward center with specks of about 0.1 mm diameter nearest RHS N79A in a background of nearest RHS 145B, claw nearest RHS 145A; abaxial between RHS 93C and RHS 93D, with claw between RHS 145B and RHS 145A.

*Keel*.—Comprised of two main lobes that are folded around stamens and pistil; fused in the distal one-third with the two main lobes having rounded apices and the bases separate and claw-like, each with a small basal rounded lobe about 2 mm long and 2 mm wide above each claw pointing toward base; margin entire; each main lobe about 19 mm long and 8 mm across in middle; blade portion to about 14 mm long and 8 mm tall; with claw to about 5 mm long and base narrowed to 1 mm wide in the proximal 2 mm.

*Keel color*.—Adaxial and abaxial claw between RHS 145C and RHS 145B; adaxial and abaxial blade nearest RHS 145C.

*Alae*.—Two; papilionaceous corolla appendage with rounded apex, claw-like base, and entire margin; with 2 mm long by 2 mm wide lobe pointing toward base and about one-third of the way from base; about 20 mm long and 7 mm tall, with the claw to 2 mm wide at base of blade and 1.5 mm wide at base, and 6 mm long; blade about 15 mm long and 7 mm wide.

*Alae color*.—Adaxial and abaxial claw nearest RHS 145C; adaxial and abaxial lobe and blade between RHS 1D and RHS 145D.

*Mature keel and upper banner*.—Between RHS 94B and RHS 93D.

Receptacle: Disk-shaped, about 4 mm diameter and 2 mm depth;

Receptacle color: Nearest RHS 147B, with glaucous bloom nearest RHS 189B;

Gynoecium: One, with superior ovary and stipe; to about 20 mm long;

*Style*.—Cylindrical; glabrous; slightly lustrous; tapered and curved near stigma, about 9 mm long and about 0.7 mm diameter above ovary; color nearest RHS 145C.

*Stigma*.—About 0.2 mm diameter; color nearest RHS 150D.

*Ovary*.—Superior above hypanthium; suspended by stipe; cylindrical; glabrous and slightly lustrous; about 6 mm long and about 1.5 mm in diameter; color nearest RHS 144A.

*Stipe*.—Cylindrical; glabrous; slightly lustrous; about 4 mm long and 0.7 mm diameter; color between RHS 145B and RHS 145C.

Androecium:

*Stamens*.—Ten.

*Filament*.—Glabrous; slightly lustrous; not united; to 21 mm in length and about 0.7 mm in diameter; slightly arcuate upward distally; color nearest RHS 145C.

*Anther*.—Dorsifixed; oblong; about 2 mm long and 1.2 mm wide; color nearest RHS 17A.

*Pollen*.—Spherical; abundant; color nearest RHS 14A.

Fruit: Bivalve inflated ellipsoidal pod; glabrous; to about 60 mm long, 19 mm across, and 13 mm thick; with thin, linear, arcuate, terminal beak extending about 8 mm long and about 1 mm thick; rounded base;

Fruit color: At maturity between RHS 200A and RHS 202A;

Seeds: To about 18 per pod, average about 10 (open pollinated); reniform; glabrous; about 4 mm long, 3 mm across and 2 mm thick; color nearest RHS N199C;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed;

It is claimed:

1. A new and distinct cultivar of *Baptisia* plant named 'Periwinkle Popsicle' as herein described and illustrated.

* * * * *